United States Patent [19]

Sakata et al.

[11] Patent Number: 5,273,908
[45] Date of Patent: Dec. 28, 1993

[54] STABILIZING METHOD FOR IMMUNO ACTIVE SUBSTANCES IMMOBILIZED ON INSOLUBLE CARRIER AND ITS USE IN PREPARATION OF REAGENT FOR MEASURING PHYSIOLOGICALLY ACTIVE SUBSTANCES

[75] Inventors: Yoshitsugu Sakata, Otsu; Yoshitaka Hamaguchi, Kiyose; Motoo Goto, Amagasaki; Shinzo Kobatake, Suita, all of Japan

[73] Assignee: Wako Pure Chemical Industries, Ltd., Osaka, Japan

[21] Appl. No.: 659,476

[22] Filed: Feb. 25, 1991

Related U.S. Application Data

[63] Continuation of Ser. No. 38,490, Apr. 13, 1987, abandoned, which is a continuation of Ser. No. 638,086, Aug. 6, 1984, abandoned.

[30] Foreign Application Priority Data

Aug. 5, 1983 [JP] Japan ................. 58-144201

[51] Int. Cl.$^5$ ................. G01N 33/543; G01N 33/544; G01N 33/551
[52] U.S. Cl. ................. 436/518; 436/524; 436/525; 436/527; 436/528; 436/531; 422/57
[58] Field of Search ............. 436/518, 524, 525, 527, 436/528, 531

[56] References Cited

U.S. PATENT DOCUMENTS

| | | | |
|---|---|---|---|
| 3,646,346 | 2/1972 | Catt | 436/817 |
| 4,210,418 | 7/1980 | Brown et al. | 436/826 X |
| 4,288,538 | 9/1981 | Groman et al. | 436/825 X |
| 4,444,880 | 4/1984 | Tom | 435/7 |

OTHER PUBLICATIONS

Sigma Chemical Company Catalog (St. Louis, Mo.) 1982, p. 102.
Chemical Abstracts 99:154814 Z, 1983 (Japanese Kokai Tokkyo Koho JP 58-123,459 published Jul. 22, 1983).

Primary Examiner—Sam Rosen
Attorney, Agent, or Firm—Armstrong, Westerman, Hattori, McLeland & Naughton

[57] ABSTRACT

An immuno active substance immobilized on a carrier and stabilized by immersing the carrier in a solution of at least one of sugars and proteins can be used for measuring a physiologically active substance even after stored for a long period of time. A preferred embodiment of the invention uses a synergistic mixture of a sugar and a protein as the stabilizing agents.

16 Claims, No Drawings

STABILIZING METHOD FOR IMMUNO ACTIVE SUBSTANCES IMMOBILIZED ON INSOLUBLE CARRIER AND ITS USE IN PREPARATION OF REAGENT FOR MEASURING PHYSIOLOGICALLY ACTIVE SUBSTANCES

This is a continuation of application Ser. No. 038,490, filed Apr. 13, 1987, which is a continuation of application Ser. No. 638,086, filed Aug. 6, 1984, both now abandoned.

This invention relates to a process for stabilizing immuno active substances immobilized on an insoluble carrier and preparation of reagents for measuring a physiologically active substance utilizing the immuno active substances stabilized by the above process as their components.

Antigen-antibody reactions have been used for measuring or detecting various physiologically active substances due to their high specificity and high sensitivity. Specifically, radioimmunoassay (hereinafter referred to as "RIA") systems have been applied to measure trace substances (e.g., hormones such as insulin, glucagon, thyroxine, etc.; high-molecular weight physiologically active substances such as immunoglobulin E (Ig E), $\alpha$-fetoprotoein, CEA (carcino embrionic antigen), etc.) in biological samples such as serum, urine, and tissue fluid, since RIA particularly allows highly sensitive measurement. But it is also true that the prevalence of RIA is limited due to some disadvantages. Reagents used in RIA are expensive and often unstable. Complicated and expensive apparatuses are required for reading the any results. Most of all, special safety standards are required for the handling of radioisotopes and disposal of radioactive wastes.

On the other hand, the enzyme immunoassay (hereinafter referred to as EIA) was introduced in 1971 in order to overcome these disadvantages in RIA. In EIA, an enzyme is used as labeling substance instead of radioactive isotope. An enzyme labeled reagent is inexpensive and stable for a long period of time. EIA has the equivalent or higher sensitivity for measurement as RIA. Further the test results can be measured by the naked eye or a simple apparatus. Due to such advantages over RIA, application of EIA is rapidly expanded. But RIA and EIA are based on the same measuring principles and only differ in their labeling substances. As to measuring systems, there have been reported various kinds of measuring systems, which can be divided into two groups, that is, the heterogeneous measuring system which employs the B/F separating method and the homogeneous measuring system which does not employ the B/F separating method. The B/F separating method indicates that a bound form of an antigen and an antibody as a result of antigen-antibody reaction (bound type, B) and a free form of an antigen and antibody (free type, F) are physically separated. Homogeneous system depends on inhibition or activation of the enzyme by one of the components (mainly antibody) after antigen-antibody reaction. Since few cases of such enzyme-hapten complex have been reported, the application of the homogeneous system is limited. Therefore, most present RIA and EIA employ the heterogeneous measuring system. In the heterogeneous measuring system, a solid phase method wherein an antigen or an antibody is immobilized on a water-insoluble carrier has been most frequently employed for the B/F separation. Although natural high-molecular compounds such as cellulose, Sepharose, agarose and dextran have been used as the water-insoluble carrier, these compounds require much time for washing procedure and centrifugational procedure, which results in becoming a major factor for causing scattering of measured values. In order to overcome these problems, inorganic materials such as glass and synthetic polymers such as polystyrene, polypropylene, poly(vinyl chloride) are recently used as a carrier in the form of tubes, beads, disks, fine particles (latex particles), microplates. By using these materials as carriers, the centrifugational procedure becomes unnecessary, and the washing procedure can be simplified remarkably. Thus, reproducibility of measured values becomes good, and employment of automated system becomes possible and is actually practiced in some assay fields. For the reasons mentioned above, establishment of useful assay system in the heterogeneous measuring system using the solid phase method depends on the quality of the carrier.

Preferable properties of the carrier are as follows:

(1) When an immuno active substance is bound to the carrier, it should retain the immunological activity.

(2) The carrier has no non-specific adsorption of components included in a test sample.

(3) The carrier has properties of binding strongly with an immuno active substance.

(4) The carrier has such properties as a surface structure which makes binding with a sufficient amount of immuno active substance possible.

(5) Handling such as washing procedure accompanied in the B/F separating procedure is simple and easy.

In order to prepare a carrier which satisfies the properties mentioned above and on which an immuno active substance is attached, not only the selection of kind of carrier but also the binding method of immuno active substance and the storing method of the carrier bound substance are subject matters for development. In RIA and EIA employing the solid phase method, an immuno active substance is immobilized on a carrier such as glass beads, polystyrene beads, by covalent bond or physical adsorption method, and the carrier bound substance is stored in a buffer solution containing serum albumin.

But such a method has many problems in that (i) it is necessary to extract the buffer solution using a filter paper at the time of use, which results in requiring much labor and causing scattering of measured values, (ii) when dried, deterioration of the solid phase takes place due to decrease of the immunological activity of immuno active substance, and (iii) there are many technical problems for designing an automated assay system.

It is an object of this invention to provide a process for stabilizing an immuno active substance immobilized on a carrier overcoming the disadvantages mentioned above, and to provide a reagent utilizing the immuno active substance thus stabilized on a carrier as its component for measuring physiologically active substances.

This invention provides a process for stabilizing an immuno active substance immobilized on a carrier, which comprises immersing a carrier bound an immuno active substance in a solution of at least one member selected from the group consisting of a sugar and a protein.

This invention also provides an assay reagent for measuring a physiologically active substance comprising as a component an immuno active substance immobilized on a carrier and stabilized by immersing the carrier bound immuno active substance in a solution of at least one member selected from the group consisting of a sugar and a protein.

As the carrier, there can be used any conventional insoluble ones usually used in RIA and EIA. Preferable carriers are insoluble (water-insoluble) ones which allow easy solid-liquid separation without conducting centrifugational separation. Examples of such insoluble carriers are synthetic polymer compounds such as polystyrene, polypropylene, poly(vinyl chloride), polyethylene, polychlorocarbonate, silicone resin, silicone rubber, etc.; inorganic materials such as porous glass, ground glass, alumina, silica gel, activated charcoal, metal oxides, etc. These materials can be used in any forms of tubes, beads, disk flakes, fine particles (latex particles), microplates, etc.

As a method for immobilizing the immuno active substance on the carrier, there can be used conventional methods such as a covalent coupling method and a physical adsorption method.

The covalent coupling method is a method for fixing an immuno active substance on a water-insoluble carrier by covalent bond. The largest number of reports deal with this covalent coupling method among carrier binding methods. The functional groups which cause the binding of the immuno active substance with the carrier are an α- or ε-amino group, an α-, β- or γ-carboxyl group, a sulfhydryl group, a hydroxyl group, an imidazole group, a phenol group, and the like. These functional groups react with a diazonium group, an acid azide, an isocyanate or an activated halogenated alkane. Therefore, by using such a reactive functional group, it becomes possible to bind the immuno active substance with the water-insoluble carrier by covalent bond (e.g. see Taisha vol. 8, page 696, 1971). In the case of using an inorganic material such as glass, the inorganic material is first treated with a trialkoxysilane derivative having a functional group such as Y-aminopropyltriethoxysilane in order to introduce a reactive functional group thereinto. The resulting amino group-containing alkylated glass thus obtained can be bound with an immuno active substance by covalent bond by the same treatment as in the case of amino group-containing immuno active substance. In general, introduction of a reactive aldehyde group by the treatment with glutaraldehyde has been widely used to couple an immuno active substance with a carrier (J. Biochem., vol. 80, p. 895, 1976). There can also be used various crosslinking agents depending on the kinds of immuno active substances. For example, there can be used succinaldehyde, malonaldehyde, or the like in addition to glutaraldehyde mentioned above for crosslinking an amino group with an amino group, m-maleimidobenzoyl-N-hydroxysuccinimide ester, 4-(maleimidomethyl)cyclohexane-1-carboxyl-N-hydroxysuccinimide ester for crosslinking an amino group with a sulfhydryl group, and o-phenylenedimaleimide for binding a sulfhydryl group with a sulfhydryl group.

The physical adsorption method is a method for immobilizing an immuno active substance on a water-insoluble carrier by physical adsorption. As the carrier, there can be used inorganic materials such as activated charcoal, porous glass, glass beads, alumina, a metal oxide, silica gel, hydroxy apatite, etc.; and synthetic polymer compounds such as polystyrene, polyethylene, poly(vinyl chloride), polypropylene, polychlorocarbonate, etc. Among them, the use of glass, polystyrene, or poly(vinyl chloride) in the form of tubes, beads, disk flakes, fine particles (latex particles), microplates are preferred.

As the immuno active substance to be immobilized on the carrier, there can be used an antigen, an antibody and a hapten (drugs, etc.).

Examples of the antigen are hormones such as insulin, glucagon, growth hormone, human chorionic gonadotropin, adrenocortical hormone, thyroid stimulating hormone, etc.; proteins such as IgG, IgM, IgA, IgE, IgD, α-fetoprotein, ferritin, $\beta_2$-microglobulin, CEA, etc.; and virus antigens such as $HB_s$ antigen, rubella virus antigen, etc.

Examples of the antibody are those obtained by immunizing a mammal such as a rabbit, a guinea pig, a mouse, a goat, a sheep or the like, or a bird such as a chicken, a duck, or the like with an antigen or a hapten mentioned below by a conventional method (e.g., antiinsulin antibody, antiglucagon antibody, anti-IgG antibody, anti-α-fetoprotein antibody, anti-$\beta_2$-microglobulin antibody, etc.).

Examples of the hapten are steroid hormones, catecholamines, and vitamins.

As the sugar solution, there can be used a solution obtained by dissolving a monosaccharide such as ribose, glucose, fructose, mannose, galactose, maltose, lactose, or the like, an oligosaccharide, or a polysaccharide such as sucrose, dextran, dextrin, or the like, these saccharides being used alone or as a mixture thereof, in purified water or a buffer solution. Among these sugar solutions, lactose, sucrose, and dextrin solutions are preferred.

As the protein solution, there can be used a solution obtained by dissolving a serum albumin such as a bovine serum albumin, a human serum albumin, a sheep serum albumin, or water-soluble gelatin, in purified water or a buffer solution. Among these protein solutions, bovine serum albumin and water-soluble gelatin solutions are preferred.

The sugar solution and the protein solution can be used alone or as a mixture thereof. When the mixed solution of sugar and protein is used, more excellent effects can be expected.

The sugar content in the sugar solution is usually 0.1 to 10 weight/volume percent, preferably 2.5 to 5 weight/volume percent.

The protein content in the protein solution is usually 0.1 to 2 weight/volume percent, preferably 0.5 to 1.5 weight/volume percent.

When the solution contains both sugar and protein, the sugar content is usually 0.1 to 10 weight/volume percent, and preferably 2.5 to 5 weight/volume percent and the protein content is usually 0.1 to 2 weight/volume percent, and preferably 0.5 to 1.5 weight/volume percent.

As the solvent for dissolving a sugar and/or a protein, there can be used purified water or a buffer solution. Examples of the buffer solution are those having buffering effect at near neutral pH such as a phosphate buffer solution, a tris-HCl buffer solution, a Good's buffer solution, and the like. Among them, the phosphate buffer solution is particularly preferred. The molar concentration of the buffer solution is usually 0.01 to 0.2 M, preferably 0.02 to 0.05 M and the pH of it is preferably 6.8 to 7.2.

When preparing the solution of sugar and/or protein, there is no limitation to the order of addition of these materials.

In order to stabilize the immuno active material immobilized on a carrier in the dried state, the carrier attaching the immuno active material is first immersed in the solution of protein and/or sugar, for example, for 20 to 40 minutes at room temperature, and dried, for example, by placing the thus treated carrier on a filter paper for a sufficient time to allow air drying. The dried carrier with stabilized immuno active substance can be used as a reagent. More preferably, the thus dried carrier is stored in a vessel sealed and capped under nitrogen gas or reduced pressure. By subjecting the carrier to immersing treatment in the solution of protein and/or sugar, decrease of the antigen or antibody activity of immuno active substance caused during air drying procedure of the carrier can be prevented effectively.

The stabilized immuno active substances immobilized on a carrier is useful as a reagent for measuring physiologically active substances in RIA or EIA.

Typical measuring systems in solid phase RIA and EIA are a competitive method and a sandwich method.

The competitive method is based on the competitive reaction between an unknown amount of the antigen in a test sample and known amount of the same radioisotopically or enzymatically labelled antigen to its antibody immobilized on the solid phase. Amount of the antigen in a test sample is quantified by measuring the solid phase bound or unbound amount of radioactivity or enzymatic activity of the labelled antigen.

On the other hand, the sandwich method is based on the reaction that two specific antibodies sandwich an unknown antigen to be measured. One of the antibodies is immobilized onto a solid phase and the other is labelled by a radioisotope or an enzyme. The amount of the antigen to be measured is quantified by measuring the bound amount of radioactivity or enzymatic activity of antibody on the solid phase.

Needless to say, the application of the present invention is not limited to the typical measuring systems in RIA and EIA mentioned above. It also can be applied to various modified systems which utilize the immuno active substance immobilized on a carrier.

This invention is illustrated in detail by way of the following Examples, wherein all percents are by weight unless otherwise specified.

Reference Example 1

(1) Preparation of Antiinsulin Antibody-Bound Glass Beads

Commercially available glass beads (6-7 mm in diameter) (500 pieces) were washed with purified water, followed by washing with acetone. Then the glass beads were immersed in a 2% γ-aminotriethoxysilane/acetone solution and stood for 3 hours at room temperature. After the reaction, the glass beads were washed with acetone and purified water successively. The amino group-containing glass beads thus obtained were activated by immersing them in a 25% glutaraldehyde solution for 2 hours at room temperature. After extensively washed with purified water, the glass beads were immersed in 100 ml of 0.02 M phosphate buffer (pH 7.3) containing 3 mg of guinea pig antiinsulin antibody and allowed to stand at 4° C. for 16 hours to bind the anti-insulin antibody to the glass beads. After the coupling reaction, the glass beads were washed with a 0.02 M phosphate buffer (pH 7.3), and stored in a phosphate buffer (pH 7.3) containing 0.15M NaCl, 1% bovine serum albumin, 1 mM EDTA (ethylenediaminetetraacetic acid) and 0.05% NaN$_3$ in a cold place until the use.

(2) Preparation of Anti-$\beta_2$-microglobulin Antibody-Bound Polystyrene Beads Commercially available polystyrene beads (6.5 mm in diameter) (500 pieces) were washed with a 0.02 M phosphate buffer (pH 7.5) and then immersed in 100 ml of a 0.02 M phosphate buffer (pH 7.5) containing 3 mg of rabbit anti-$\beta_2$-microglobulin antibody and allowed to stand at 4° C. for 16 hours to bind the anti-$\beta_2$-microglobulin antibody to the polystyrene beads. After the reaction, the polystyrene beads were washed with a 0.02 M phosphate buffer (pH 7.3), stored in a 0.02 M phosphate buffer (pH 7.3) containing 0.15 M NaCl, 1% bovine serum albumin, 1 mM EDTA and 0.05% NaN$_3$ in a cold place until the use.

(3) Preparation of Anti-C-Reactive Protein (C-RP) Antibody-Bound Poly(vinyl chloride) Plates To each well of commercially available poly(vinyl chloride) microplates (U type, 96 wells), 0.1 ml of a 0.05 M carbonate buffer (pH 9.6) containing 5 μg of mouse anti-C-RP antibody was added and allowed to stand at 4° C. for 21 hours to bind the anti-C-RP antibody to the microplates. After the reaction, each well was washed with a 0.01 M phosphate buffer (pH 7.4) containing 0.05% polyoxyethylene sorbitan monolauryl ether (Tween 20, a trade name, manufactured by Kao-Atlas Co., Ltd.), added with 0.2 ml of a 0.01 M phosphate buffer (pH 7.4) containing 1% bovine serum albumin, allowed to stand at 4° C. for 19 hours, and stored in a cold place until the use.

(4) Preparation of Anti-CEA Antibody-Bound Glass Beads

Commercially available 500 glass beads (6-7 mm in diameter) were washed with purified water, followed by washing with acetone. Then the glass beads were immersed in a 2% γ-aminotriethoxysilane/acetone solution and stood for 3 hours at room temperature. After the reaction, the glass beads were washed with acetone and purified water successively. The glass beads thus obtained were activated by immersing in a 25% glutaraldehyde solution for 2 hours at room temperature. After extensively washed with purified water, the glass beads were immersed in 100 ml of 0.02 M phosphate buffer (pH 7.3) containing 3 mg of rabbit antibody and stood for 16 hours at 4° C. to bind the anti CEA antibody to the glass beads. After the coupling reaction, the glass beads were washed with 0.02 M phosphate buffer (pH 7.3) and stored in 0.02 M phosphate buffer (pH 7.3) containing 0.15 M NaCl, 1% bovine serum albumin, 1 mM EDTA and 0.05% NaN$_3$ in a cold place until the use.

Reference Example 2

[1] Measurement of Insulin by EIA Method Using Antiinsulin Antibody-Bound Glass Beads Measurement of Insulin by EIA
Reagents
(1) Antiinsulin antibody-bound glass beads obtained in Reference Example 1.
(2) Standard insulin of 0 to 320 μU/ml,
(3) Peroxidase labeled antiinsulin antibody.
(4) A 0.02 M phosphate buffer (pH 6.9) containing 0.15 M NaCl, 1% bovine serum albumin, 1 mM EDTA and 0.1% sodium salicylate for diluting the above-mentioned reagents (2) and (3).

(5) 60 mg of o-phenylenediamine.
(6) 1.7 v/v% hydrogen peroxide solution.
(7) A 0.05 M citrate-0.1 M phosphate buffer (pH 4.8). for dissolving the enzyme substrates of (5) and (6) mentioned above.
(8) 1.5 N $H_2SO_4$.
(9) A color developing reagent solution in an amount of 20 ml containing 60 mg of o-phenylenediamine and 200 μl of hydrogen peroxide obtained by dissolving the above-mentioned (5) and (6) in (7).

Assay Procedures

To 500 μl of the reagent (3) diluted with the reagent (4), 50 μl of standard insulin solution was added, followed by addition of the reagent (1) to conduct the reaction at 37° C. for 60 minutes. After the reaction, the beads were washed with 0.9% NaCl, followed by the addition of 500 μl of the reagent (9) to start the enzymatic reaction. After incubating at 37° C. for 15 minutes, 3.0 ml of the reagent (8) was added to stop the reaction and absorbance of the reaction mixture was measured at 492 nm.

[2] Measurement of $\beta_2$-Microglobulin by EIA Method Using

Anti-$\beta_2$-microglobulin Antibody-Bound Polystyrene Beads Measurement of $\beta_2$-Microglobulin by EIA Reagents (1) Anti-$\beta_2$-microglobulin antibody-bound polystyrene beads obtained in Reference Example 1.
(2) Standard $\beta_2$-microglobulin of 0 to 200 μg/l.
(3) Peroxidase labeled anti-$\beta_2$-microglobulin antibody.
(4) A 0.02 M phosphate buffer (pH 6.9) containing 0.15 M NaCl, 1% bovine serum albumin, 1 mM EDTA, and 0.1% sodium salicylate for diluting the above-mentioned reagents (2) and (3).
(5) 60 mg of o-phenylenediamine.
(6) 1.7 v/v% hydrogen peroxide solution.
(7) A 0.05 M citrate-0.1 M phosphate buffer (pH 4.8), for dissolving the enzyme substrates of (5) and (6) mentioned above.
(8) 1.5 N $H_2SO_4$.
(9) A color developing reagent solution in an amount 20 of 20 ml containing 60 mg of o-phenylenediamine and 200 μl of hydrogen peroxide obtained by dissolving the above-mentioned (5) and (6) in (7).

Assay Procedures

To 1 ml of the reagent (3) diluted with the reagent (4), 20 μl of standard $\beta_2$-microglobulin was added, followed by addition of the reagent (1) to conduct the reaction at 37° C. for 60 minutes. After the reaction, the beads were washed with 0.9% NaCl, followed by the addition of 500 μl of the reagent (9) to start the enzymatic reaction. After incubating at 37° C. for 15 minutes, 3.0 ml of the reagent (8) was added to stop the reaction and absorbance of the reaction mixture was measured at 492 nm.

[3] Measurement of C-RP by EIA Method Using Anti-C-RP

Antibody-Bound Poly(vinyl chloride) Plates Measurement of C-RP by EIA

Reagents (1) Anti-C-RP antibody-bound poly(vinyl chloride) plates obtained in Reference Example 1.
(2) Standard C-RP of 0 to 1000 ng/ml.
(3) Peroxidase labeled anti-C-RP antibody.
(4) A 0.02 M phosphate buffer (pH 7.3) containing 1% bovine serum albumin, 0.5% polyoxyethylene nonylphenyl ether (Nonipol 300, a trade name, manufactured by Sanyo Chemical Industries, Ltd.) and 0.9% NaCl for diluting the above-mentioned reagents (2) and (3).
(5) 60 mg of o-phenylenediamine.
(6) 1.7 v/v% hydrogen peroxide solution.
(7) A 0.05 M citrate-0.1 M phosphate buffer (pH 4.8). for dissolving the enzyme substrates of (5) and (6) mentioned above.
(8) 6N $H_2SO_4$.
(9) A color developing reagent solution in an amount of 20 ml containing 60 mg of o-phenylenediamine and 200 μl of hydrogen peroxide obtained by dissolving the above-mentioned (5) and (6) in (7).

Assay Procedures

To each well, 100 μl of standard C-RP diluted with the reagent (4) was added and allowed to stand at 37° C. for 120 minutes. Then, the reaction solution was removed by suction and each well was washed with the reagent (4) extensively. After adding 100 μl of the reagent (3), the reaction was conducted at 37° C. for 120 minutes. After the reaction, each well was washed with the reagent (4), followed by addition of 100 μl of the reagent (9) to start the enzymatic reaction. After incubating at room temperature for 15 minutes, 50 μl of the reagent (8) was added to stop the reaction and absorbance of the reaction mixture was measured at 490 nm by using a colorimeter for microplates.

[4] Measurement of CEA by EIA

Reagents (1) Anti CEA antibody-bound glass beads obtained in Reference Example 1.
(2) Standard CEA of 60 μg/ml.
(3) Peroxidase labeled anti CEA antibody.
(4) A 0.02 M phosphate buffer (pH 7.0) containing 0.15 M NaCl, 1% bovine serum albumin, 1 mM EDTA and 0.1% sodium salicylate for diluting the above-mentioned reagents (2) and (3).
(5) 60 mg of o-phenylenediamine.
(6) 1.7 v/v% hydrogen peroxide solution,
(7) A 0.05 M citrate-0.1 M phosphate buffer (pH 4.8) for dissolving the enzyme substrates of (5) and (6) mentioned above.
(8) 1.5 N $H_2SO_4$.
(9) A color developing reagent solution in an amount of 20 ml containing 60 mg of o-phenyelenediamine and 200 μl of 1.7% hydrogen peroxide obtained by dissolving the above mentioned (5) and (6) in (7).

Assay procedures

To 500 μl of the reagent (3) diluted with the reagent (4), 50 μl of standard CEA solution was added, followed by addition of the reagent (1) to conduct the reaction at 37° C. for 18 hours. After the reaction, the beads were washed with 0.9% NaCl followed by the addition of 500 μl of the reagent (9) to start the enzymatic reaction. After incubating at 37° C. for 30 minutes, 3 ml of the reagent (8) was added to stop the reaction and absorbance of the reaction mixture was measured at 492 nm.

EXAMPLE 1

Stabilization of Antiinsulin Antibody-Bound Glass Beads

After washing the antiinsulin antibody-bound glass beads prepared in Reference Example 1 with purified water, the glass beads were immersed in the following treating solutions (a) to (e) at room temperature for 30 to 40 minutes.

(a) A 0.02 M phosphate buffer (pH 6.9) containing 5 w/v% sucrose and 1% bovine serum albumin.

(b) A 0.02 M phosphate buffer (pH 6.9) containing 5 w/v% sucrose.

(c) A 0.02 M phosphate buffer (pH 6.9) containing 1% bovine serum albumin.

(d) A 0.02 M phosphate buffer (pH 6.9) containing 1% water-soluble gelatin.

(e) A 0.02 M phosphate buffer (pH 6.9).

After the treatment, the glass beads were air dried at room temperature.

The glass beads thus obtained were subjected to a severe test by storing the glass beads in a constant temperature chamber at 40° C. Stability of the antibody-bound glass beads were evaluated as follows. A sample containing 320 μU/ml of insulin was measured by EIA method described in Reference Example 2 and stability of the glass beads was evaluated in terms of activity retention rate (%) compared with the measured value obtained by using control glass beads. The control glass beads were prepared as described in Reference Example 1 and stored at 4° C. in the immersed state.

The results were shown in Table 1.

TABLE 2

| Treating solution | Activity retention rate (%) | |
|---|---|---|
| | Stored for 2 weeks | Stored for 4 weeks |
| Control | 100 | 100 |
| (a) | 94 | 189 |
| (b) | 70 | 68 |
| (c) | 47 | 19 |
| (d) | 71 | 66 |
| (e) | 14 | 9 |

EXAMPLE 2

Stabilization of Anti-$\beta_2$-microglobulin Antibody-Bound Polystyrene Beads

The anti-$\beta_2$-microglobulin antibody-bound polystyrene beads prepared in Reference Example 1 were immersed in purified water. After removing water on a filter paper, the polystyrene beads were immersed in the following treating solutions (a) to (e) at room temperature for 30 to 40 minutes.

(a) A 0.02 M phosphate buffer (pH 6.9) containing 5 w/v% sucrose and 1% bovine serum albumin.

(b) A 0.02 M phosphate buffer (pH 6.9) containing 5 w/v% sucrose.

(c) A 0.02 M phosphate buffer (pH 6.9) containing 1% bovine serum albumin.

(d) A 0.02 M phosphate buffer (pH 6.9) containing 1% water-soluble gelatin.

(e) A 0.02 M phosphate buffer (pH 6.9).

After the treatment, the polystyrene beads were taken out from the solutions and placed on a filter paper to remove the water and air dried at room temperature.

The polystyrene beads thus treated were subjected to the severe test in the same manner as described in Example 1 by storing them in the constant temperature chamber at 40° C. Stability of the antibody-bound polystyrene beads were evaluated as follows. A sample containing 200 μg/l of $\beta_2$-microglobulin was measured by EIA method described in Reference Example 2 and evaluated in terms of activity retention rate (%) compared with the measured value obtained by using control polystyrene beads. The control polystyrene beads were prepared as described in Reference Example 1 and stored at 4° C. in the immersed state.

The results were shown in Table 2.

TABLE 2

| Treating solution | Activity retention rate (%) | |
|---|---|---|
| | Stored for 2 weeks | Stored for 4 weeks |
| Control | 100 | 100 |
| (a) | 102 | 101 |
| (b) | 93 | 81 |
| (c) | 81 | 42 |
| (d) | 80 | 79 |
| (e) | 42 | 37 |

EXAMPLE 3

Stabilization of Anti-CRP Antibody-Bound Poly(vinyl chloride) Microplates

The anti-CRP antibody-bound poly(vinyl chloride) microplates prepared in Reference Example 1 were treated by using the following solutions and procedures.

(a) 4% Lactose solution was poured into each well of microplates and then each well was dried.

(b) 0 02 M Hepes buffer (pH 7.0) containing 1% bovine serum albumin was poured in each well of microplates and then each well was dried.

(c) 0.01 M Phosphate buffer (pH 7.4) containing 1% bovine serum albumin was poured in each well of microplates and stored in the poured state.

(d) Each well was air dried without treatment.

After the treatment, microplates were stored at 25° C. for 7 weeks. Stability of the antibody-bound microplates was evaluated as follows. A sample containing 1000 μg/ml CRP was measured by EIA method described in Reference Example 2 and evaluated in terms of activity retention rate (%) compared with the measured value obtained by control microplates which were prepared in the same manner as described in Reference Example 1 at the time of use. The results were shown in Table 3.

TABLE 3

| Treating procedures | Activity retention rate (%) |
|---|---|
| Control | 100 |
| (a) | 95 |
| (b) | 90 |
| (c) | 89 |
| (d) | 0 |

EXAMPLE 4

After washing the anti CEA antibody-bound glass beads prepared in Reference Example 1 with purified water, the glass beads were immersed in the following solutions (a) to (h) at room temperature for 30 to 40 minutes.

(a) A 0.02 M phosphate buffer (pH 7.0) containing 5% sucrose and 1% bovine serum albumin.

(b) A 0.02 M phosphate buffer (pH 7.0) containing 5% lactose.

(c) A 0.02 M tris-HCl buffer (pH 7.2) containing 5% mannose and 1.5% water-soluble gelatine.

(d) A 0.02 M tris-HCl buffer (pH 7.2) containing 4% dextrin.

(e) A 0.02 M Hepes buffer (pH 7.2) containing 5% sucrose.

(f) A 0.02 M phosphate buffer (pH 7.0).

(g) A 0.02 M tris-HCl buffer (pH 7.2).

(h) A 0.02 M Hepes buffer (pH 7.2).

After the treatment, the glass beads were air dried at room temperature.

The glass beads thus obtained were subjected to a severe test by storing them in a constant chamber at 40° C. Stability of the antibody-bound glass beads were evaluated as follows. A sample containing 60 μg/ml CEA was measure by EIA method described in Reference Example 2. The stability of the glass beads was evaluated in terms of activity retention rate (%) compared with the measured value obtained by using control glass beads. The control glass beads were prepared as described in Reference Example 1 and stored at 4° C. in the immersed state.

The results were shown in Table 4.

TABLE 4

| Treating solution | Activity retention rate (%) | |
|---|---|---|
| | Stored for 2 weeks | Stored for 4 weeks |
| Control | 100 | 100 |
| (a) | 98 | 92 |
| (b) | 75 | 70 |
| (c) | 92 | 85 |
| (d) | 70 | 65 |
| (e) | 83 | 76 |
| (f) | 15 | 6 |
| (g) | 12 | 3 |
| (h) | 20 | 11 |

What is claimed is:

1. A process for stabilizing an immuno active substance immobilized on a carrier, consisting essentially of immersing a carrier bound immuno active substance in a synergistic solution of a sugar and a protein and air drying the immersed carrier.

2. A process according to claim 1, wherein the carrier is a synthetic polymer material or an inorganic substance.

3. A process according to claim 1, wherein the immuno active substance is an antigen.

4. A process according to claim 1, wherein the immuno active substance is an antibody.

5. A process according to claim 2, wherein the inorganic substance is glass, silica gel or a metal oxide.

6. A process according to claim 2, wherein the synthetic polymer material is polystyrene, polyethylene, polypropylene or poly(vinyl chloride).

7. A process according to claim 1, wherein the protein is a water-soluble gelatin.

8. A process according to claim 1, wherein the sugar is ribose, glucose, fructose, mannose, galactose, maltose, lactose, sucrose, dextrin, dextran or a mixture thereof.

9. A process according to claim 1, wherein the sugar is sucrose, lactose or dextrin, and the protein is serum albumin or water-soluble gelatin.

10. A process according to claim 1, wherein the solution is a solution of a sugar and a solution of water-soluble gelatin.

11. A reagent for measuring a physiologically active substance consisting essentially of an immuno active substance immobilized on a carrier and stabilized by immersing the carrier bound immuno active substance in a synergistic solution of a sugar and a protein, followed by air drying.

12. A reagent according to claim 11, wherein the carrier is an inorganic substance.

13. A reagent according to claim 11, wherein the carrier is a synthetic polymer material.

14. A reagent according to claim 11, wherein the immuno active substance is an antibody.

15. A reagent according to claim 11, wherein the solution is a solution of a sugar and a solution of a water-soluble gelatin.

16. A process for measuring a physiologically active substance by enzyme immunoassay or radioimmunoassay comprising combining the substance to be measured with a reagent consisting essentially of an immuno active substance immobilized on a carrier and stabilized by immersing the carrier bound immuno active substance in a synergistic solution of a sugar and a protein, followed by air drying, and determining the results.

* * * * *